United States Patent
Moore, Jr. et al.

(10) Patent No.: US 8,293,795 B1
(45) Date of Patent: Oct. 23, 2012

(54) PREPARATION OF CONCENTRATED AQUEOUS BROMINE SOLUTIONS AND BIOCIDAL APPLICATIONS THEREOF

(75) Inventors: Robert M. Moore, Jr., Baton Rouge, LA (US); Christopher J. Nalepa, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 550 days.

(21) Appl. No.: 09/451,319

(22) Filed: Nov. 30, 1999

Related U.S. Application Data

(63) Continuation-in-part of application No. 09/088,300, filed on Jun. 1, 1998, now Pat. No. 6,068,861.

(51) Int. Cl.
*A01N 41/06* (2006.01)
*A61K 31/18* (2006.01)

(52) U.S. Cl. .................................................. 514/601

(58) Field of Classification Search .................. 424/703
See application file for complete search history.

(56) References Cited

U.S. PATENT DOCUMENTS

| | | | |
|---|---|---|---|
| 3,152,073 A | 10/1964 | Morton | 210/62 |
| 3,170,883 A | 2/1965 | Owen et al. | 252/187 |
| 3,308,062 A | 3/1967 | Gunther | 210/58 |
| 3,328,294 A | 6/1967 | Self et al. | 210/62 |
| 3,558,503 A * | 1/1971 | Goodenough et al. | 252/187 |
| 3,589,859 A | 6/1971 | Foroulis | 21/2.7 |
| 3,711,246 A | 1/1973 | Foroulis | 21/2.7 |
| 3,749,672 A | 7/1973 | Golton et al. | 252/95 |
| 3,767,586 A | 10/1973 | Rutkiewic | 252/187 H |
| 4,032,460 A | 6/1977 | Zilch et al. | 252/8.55 B |
| 4,237,090 A | 12/1980 | DeMonbrun et al. | 422/13 |
| 4,295,932 A | 10/1981 | Pocius | 162/161 |
| 4,382,799 A | 5/1983 | Davis et al. | 8/107 |
| 4,427,435 A | 1/1984 | Lorenz et al. | 71/67 |
| 4,451,376 A | 5/1984 | Sharp | 210/701 |
| 4,465,598 A | 8/1984 | Darlington et al. | 210/721 |
| 4,476,930 A | 10/1984 | Watanabe | 166/279 |
| 4,490,308 A | 12/1984 | Fong et al. | 260/513 N |
| 4,539,071 A | 9/1985 | Clifford et al. | 162/161 |
| 4,546,156 A | 10/1985 | Fong et al. | 526/240 |
| 4,566,973 A | 1/1986 | Masler, III et al. | 210/701 |
| 4,595,517 A | 6/1986 | Abadi | 252/82 |
| 4,595,691 A | 6/1986 | LaMarre et al. | 514/367 |
| 4,604,431 A | 8/1986 | Fong et al. | 525/351 |
| 4,642,194 A | 2/1987 | Johnson | 210/699 |
| 4,643,835 A | 2/1987 | Koeplin-Gall et al. | 210/754 |
| 4,661,503 A | 4/1987 | Martin et al. | 517/372 |
| 4,680,339 A | 7/1987 | Fong | 525/54.11 |
| 4,680,399 A | 7/1987 | Buchardt | 546/139 |
| 4,703,092 A | 10/1987 | Fong | 525/351 |
| 4,711,724 A | 12/1987 | Johnson | 210/699 |
| 4,752,443 A | 6/1988 | Hoots et al. | 422/13 |
| 4,759,852 A | 7/1988 | Trulear | 210/699 |
| 4,762,894 A | 8/1988 | Fong et al. | 525/344 |
| 4,777,219 A | 10/1988 | Fong | 525/329.4 |
| 4,801,388 A | 1/1989 | Fong et al. | 210/701 |
| 4,802,990 A | 2/1989 | Inskeep, Jr. | 210/699 |
| 4,822,513 A | 4/1989 | Corby | 52/106 |
| 4,846,979 A * | 7/1989 | Hamilton | 210/754 |
| 4,883,600 A | 11/1989 | MacDonald et al. | 210/696 |
| 4,886,915 A | 12/1989 | Favstritsky | 564/503 |
| 4,898,686 A | 2/1990 | Johnson et al. | 252/389.2 |
| 4,906,651 A | 3/1990 | Hsu | 514/372 |
| 4,923,634 A | 5/1990 | Hoots et al. | 252/389.2 |
| 4,929,424 A | 5/1990 | Meier et al. | 422/9 |
| 4,929,425 A | 5/1990 | Hoots et al. | 422/13 |
| 4,966,716 A | 10/1990 | Favstritsky et al. | 210/755 |
| 4,992,209 A | 2/1991 | Smyk et al. | 252/387 |
| 4,995,987 A | 2/1991 | Whitekettle et al. | 210/754 |
| 5,034,155 A | 7/1991 | Soeder et al. | 252/389.23 |
| 5,035,806 A | 7/1991 | Fong et al. | 210/701 |
| 5,047,164 A | 9/1991 | Corby | 252/106 |
| 5,055,285 A | 10/1991 | Duncan et al. | 423/473 |
| 5,118,426 A | 6/1992 | Duncan et al. | 210/721 |

(Continued)

FOREIGN PATENT DOCUMENTS

| | | |
|---|---|---|
| EP | 1080641 A2 | 3/2001 |
| WO | 9015780 | 12/1990 |
| WO | 96/14092 A1 | 5/1996 |
| WO | 9720546 | 6/1997 |
| WO | 9720909 | 6/1997 |
| WO | 9734827 | 9/1997 |
| WO | 9743392 | * 11/1997 |
| WO | 9815609 | 4/1998 |
| WO | 9906320 | 2/1999 |
| WO | 9932596 | 7/1999 |
| WO | 9955627 | 11/1999 |
| WO | 00/34186 | 6/2000 |

OTHER PUBLICATIONS

Ault et al., "Infrared and Raman Spectra of the $M+Cl_3^-$ ion Pairs and Their Chlorine-bromine Counterparts isolated in Argon Matrices", Journal of Chemical Physics, 1976, vol. 64, No. 12, pp. 4853-4859.

*Primary Examiner* — Alton Pryor

(74) *Attorney, Agent, or Firm* — Marcy M. Hoefling

(57) ABSTRACT

A process of producing a concentrated liquid biocide formulation is described. Mixed together are (a) bromine and (b) an aqueous solution of alkali metal salt of sulfamic acid having a pH of at least about 12, in amounts such that (i) the active bromine content of the solution is at least about 100,000 ppm (wt/wt), and (ii) the atom ratio of nitrogen to active bromine from (a) and (b) is greater than 1. A continuous process for producing the concentrated liquid biocide composition is provided. This process comprises continuously feeding into mixing apparatus (i) bromine and (ii) an aqueous solution of alkali metal salt of sulfamic acid; the desired product is withdrawn from the mixing apparatus at a rate sufficient to enable the continuous feeding to be maintained. Also described are methods for disinfecting surfaces and for sanitizing bodies of water using a single-feed, bromine-based biocide. These methods use concentrated liquid biocide compositions comprising biocidally active bromine as the biocide.

21 Claims, No Drawings

U.S. PATENT DOCUMENTS

| | | | |
|---|---|---|---|
| 5,120,452 A | 6/1992 | Ness et al. | 210/754 |
| 5,120,797 A | 6/1992 | Fong et al. | 525/329.4 |
| 5,141,652 A | 8/1992 | Moore, Jr. et al. | 210/754 |
| 5,179,173 A | 1/1993 | Fong et al. | 525/329.4 |
| 5,192,459 A | 3/1993 | Tell et al. | 252/106 |
| 5,194,238 A | 3/1993 | Duncan et al. | 423/473 |
| 5,196,126 A | 3/1993 | O'Dowd | 210/754 |
| 5,202,047 A | 4/1993 | Corby | 252/106 |
| 5,259,985 A | 11/1993 | Nakanishi et al. | 252/180 |
| 5,264,136 A | 11/1993 | Howarth et al. | 210/754 |
| 5,389,384 A | 2/1995 | Jooste | 424/661 |
| 5,414,652 A | 5/1995 | Mieda et al. | 365/122 |
| 5,424,032 A | 6/1995 | Christensen et al. | 422/14 |
| 5,443,849 A | 8/1995 | Corby | 424/667 |
| 5,464,636 A | 11/1995 | Hight et al. | 424/661 |
| 5,525,241 A | 6/1996 | Clavin et al. | 210/753 |
| 5,527,547 A | 6/1996 | Hight et al. | 424/661 |
| 5,589,106 A | 12/1996 | Shim et al. | 252/387 |
| 5,607,619 A | 3/1997 | Dadgar et al. | 252/187.2 |
| 5,679,239 A | 10/1997 | Blum et al. | 205/556 |
| 5,683,654 A | 11/1997 | Dallmier et al. | 422/14 |
| 5,795,487 A | 8/1998 | Dallmier et al. | 210/754 |
| 5,900,512 A | 5/1999 | Elnagar et al. | 568/14 |
| 5,922,745 A | 7/1999 | McCarthy et al. | 514/372 |
| 5,942,126 A | 8/1999 | Dallmier et al. | 210/756 |
| 6,007,726 A | 12/1999 | Yang et al. | 210/752 |
| 6,015,782 A | 1/2000 | Petri et al. | 510/379 |
| 6,037,318 A | 3/2000 | Na et al. | 510/379 |
| 6,068,861 A * | 5/2000 | Moore et al. | 424/703 |
| 6,110,387 A * | 8/2000 | Choudhury et al. | 210/752 |
| 6,123,870 A | 9/2000 | Yang et al. | 252/186.1 |
| 6,156,229 A | 12/2000 | Yang et al. | 252/186.1 |
| 6,270,722 B1 | 8/2001 | Yang et al. | 422/37 |
| 6,287,473 B1 | 9/2001 | Yang et al. | 210/754 |

* cited by examiner

PREPARATION OF CONCENTRATED AQUEOUS BROMINE SOLUTIONS AND BIOCIDAL APPLICATIONS THEREOF

REFERENCE TO RELATED APPLICATIONS

This is a continuation-in-part of commonly-owned Continued Prosecution Application (CPA) Ser. No. 09/088,300, filed Jun. 1, 1998 now U.S. Pat. No. 6,068,861, issued May 30, 2000, which continues the prosecution of prior commonly-owned copending application Ser. No. 09/088,300, filed Jun. 1, 1998.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine based biocides into a water system is through the use of aqueous NaBr in conjunction with NaOCl bleach. The user feeds both materials to a common point whereupon the NaOCl oxidizes the bromide ion to $HOBr/OBr^{\ominus}$. This activated solution is then introduced directly into the water system to be treated. The feeding of the two liquids in this fashion is necessary because the $HOBr/OBr^{\ominus}$ mixture is unstable and has to be generated on-site just prior to its introduction to the water. Furthermore, the feeding and metering of two liquids is cumbersome, especially as the system has to be designed to allow time for the activation of bromide ion to occur. Consequently, many biocide users have expressed the need for a single-feed, bromine-based biocide. Elemental bromine has been considered to meet these demands. It is a liquid at room temperature and can be fed directly to the water system, where immediate hydrolysis occurs to yield HOBr.

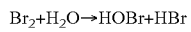

$$Br_2 + H_2O \rightarrow HOBr + HBr$$

Bromine is a fuming, dark red liquid, with a boiling point of 59° C., and a vapor pressure of 214 mm at 25° C. It corrodes most metals in the presence of water.

It can be seen that certain characteristics of this material—especially its corrosiveness, high vapor pressure and fuming tendency—necessitate care and skill in its handling and use. Early efforts to overcome the deficiencies of this material comprised complexing bromine with excess bromide ion in the presence of strong acid and stabilizing the resultant solutions with ethanolamine. The resultant solutions of ethanolammonium hydrogen perbromide contained up to 38% by weight elemental bromine. See in this connection, Faystritsky, U.S. Pat. No. 4,886,915; and Faystritsky, Hein, and Squires, U.S. Pat. No. 4,966,716.

These solutions permitted introduction of bromine to a water system using a single feed. As in the case of bromine and bromine chloride, the ethanolammonium hydrogen perbromide hydrolyzed in water to release HOBr. The vapor pressures of these solutions were lower than elemental bromine and bromine chloride. Nevertheless, the solutions still possessed measurable vapor pressures, and thus tended to produce undesirable reddish-colored vapors during storage and use.

An economically acceptable way of stabilizing high concentrations of aqueous solutions of bromine chloride is described in U.S. Pat. No. 5,141,652 to Moore, et al. The solution is prepared from bromine chloride, water and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

Many solid bromine derivatives such as BCDMH (1,3-bromochloro-5,5-dimethylhydantoin) are limited in the amount of material that can be dissolved in water and fed as a liquid to the water treatment system. For example, the solubility of BCDMH in water is only around 0.15%. Another limitation of such derivatives is that at neutral pH, HOBr rapidly decomposes, eventually forming bromide ions. Thus, the ability to store and transport these aqueous solutions is greatly limited and of questionable commercial feasibility.

U.S. Pat. No. 3,558,503 to Goodenough et al. describes certain aqueous bromine solutions stabilized with various stabilizing agents and various uses to which such solutions can be put. The compositions described in the patent comprise an aqueous bromine solution having from about 0.01 to about 100,000 parts per million by weight of bromine values wherein the molar ratio of bromine to nitrogen present in the bromine stabilizer ranges from about 2.0 to 1 to about 0.5 to 1. The stabilizer used is biuret, succinimide, urea, a lower aliphatic mono- or disubstituted urea containing from about 2 to about 4 carbon atoms in each substituent group, sulfamic acid, or an alkyl sulfonamide of the formula $RSO_3NH_2$ where R is a methyl or ethyl group. The solution also contains sufficient hydroxide additive to provide a pH in the solution ranging from about 8 to about 10, the hydroxide additive being an alkaline earth hydroxide or an alkali metal hydroxide.

U.S. Pat. No. 5,683,654 to Dallmier et al. discusses the preparation of aqueous alkali metal or alkaline earth metal hypobromite solutions by mixing an aqueous solution of alkali or alkaline earth metal hypochlorite with a water soluble bromide ion source to form a solution of unstabilized alkali or alkaline earth metal hypochlorite. To this solution is added an aqueous solution of an alkali metal sulfamate having a temperature of at least 50° C. and in an amount that provides a molar ratio of alkali metal sulfamate to alkali or alkaline earth metal hypobromite of from about 0.5 to about 6 whereby a stabilized aqueous alkali or alkaline earth metal hypobromite solution is formed. The Dallmier et al. patent teaches that much higher levels of available halogen for disinfection were attained by this approach as compared to the Goodenough et al. approach. But the Dallmier et al. patent acknowledges that in their process, the stabilization must occur quickly after the unstable NaOBr is formed.

Thus, there is a need for a water-soluble bromine-based biocide that is non-acidic and noncorrosive. There also remains a need for methods of disinfecting surfaces and of sanitizing bodies of water using a single-feed, bromine-based biocide that is water-soluble, non-acidic, and noncorrosive.

THE INVENTION

This invention involves a new process of forming concentrated aqueous solutions of biocidally active bromine and in so doing, provides novel and eminently useful concentrated aqueous biocidal solutions of bromine. This invention enables the process to be carried out not only in a commercially-feasible manner, but in addition, in an exceptionally efficient manner on a continuous basis. This invention further provides methods for disinfecting surfaces and for sanitizing bodies of water using a single-feed, bromine-based biocide. Examples of surfaces that may be disinfected using the methods of this invention include kitchen counters, bathroom counters, walls, and floors. The bodies of water that may be sanitized using the methods of this invention include cooling water systems, waste water effluents, pulp and paper mills, oilfields, air washers, fire reservoirs, and evaporative condensers. These methods use concentrated liquid biocide compositions comprising biocidally active bromine as the single-feed, bromine-based biocide.

In one of its embodiments this invention provides a process of producing a concentrated liquid biocide composition which comprises mixing (a) bromine with (b) an aqueous solution of alkali metal salt of sulfamic acid (preferably the sodium salt), the solution having a pH of at least about 12, e.g., in the range of about 12 to about 14, and preferably in the range of 12 to about 13.5. The amounts of (a) and (b) used are such that (i) the content of active bromine in the solution is at least 100,000 ppm (wt/wt) and (ii) the atom ratio of nitrogen to active bromine from (a) and (b) is greater than 1. In a preferred embodiment, the aqueous solution of alkali metal salt of sulfamic acid used in the process is preformed by mixing together in water, (i) sulfamic acid and/or an alkali metal salt of sulfamic acid, and (ii) alkali metal base in proportions such that an aqueous solution of alkali metal salt of sulfamic acid is formed having a pH of at least 12. If sulfamic acid itself is used as the starting material, it is used initially as a slurry in water with which the alkali metal base is mixed.

The above and other embodiments of this invention will be still further apparent from the ensuing description and appended claims.

In a preferred process for producing the concentrated liquid biocide composition, the aqueous solution of alkali metal salt of sulfamic acid used in the process is preformed by mixing together in water, (i) sulfamic acid and/or an alkali metal salt of sulfamic acid, and (ii) alkali metal base in proportions such that an aqueous solution of alkali metal salt of sulfamic acid is formed having a pH of at least 12. If sulfamic acid itself is used as the starting material, it is used initially as a slurry in water with which the alkali metal base is mixed. It is preferred that the alkali metal salt of sulfamic acid is the lithium, sodium, or potassium salt; more preferred are the sodium and potassium salts. Highly preferred as the alkali metal salt of sulfamic acid is the sodium salt.

When mixing bromine with the aqueous solution of alkali metal salt of sulfamic acid, it is desirable to maintain the desired pH of the resulting solution at about 12 or above by also introducing into the solution (continuously or intermittently, as desired) additional alkali metal base, such as by a co-feed of an aqueous solution of alkali metal base.

By utilizing bromine with caustic in the stabilized bromine composition, higher levels of active halogen are achievable, compared to the levels obtained by the addition of sodium hypochlorite to sodium bromide. The process and the compositions formed also have about twice the content of active bromine as the most concentrated solutions produced pursuant to the Goodenough, et al. patent. Moreover, even at the high levels of active bromine that exist in the compositions of this invention, it has been found possible to provide biocidal compositions that maintain these high levels of active bromine for at least a two-month period, and that do not exhibit a visible or offensive vapor or odor during this period.

It has now been found that sulfamate-containing solutions of bromine made with a pH between about 7 and about 11.5 do not maintain that pH over time. Rather, the pH of such solutions drifts to an acidic value. A pH of at least about 12 is thus necessary to preserve the non-acidity of solutions comprising bromine and sulfamate.

Another embodiment of this invention is an aqueous biocide composition comprising water having in solution therein (i) an active bromine content derived from bromine of at least about 100,000 ppm (wt/wt), (ii) an alkali metal salt of sulfamic acid (preferably the sodium salt), and (iii) an alkali metal bromide (preferably sodium bromide), wherein the relative proportions of (i) and (ii) are such that the atom ratio of nitrogen to active bromine is greater than 1, and wherein the pH of the composition is at least 12, e.g., in the range of about 12 to about 14, and preferably in the range of 12 to about 13.5.

In each of the embodiments of this invention, the atom ratio of nitrogen to active bromine is preferably in the range of about 1.1 to about 1.5. Still higher ratios can be employed, if desired.

In another of its embodiments this invention provides a process of producing a concentrated liquid biocide composition which process comprises:

A) continuously feeding into mixing apparatus (i) bromine and (ii) an aqueous solution of alkali metal salt of sulfamic acid (preferably a sodium salt of sulfamic acid), proportioned to produce an aqueous product having an active bromine content of at least 100,000 ppm (wt/wt), and an atom ratio of nitrogen to active bromine from (i) and (ii) greater than 1, and B) withdrawing said product from said mixing apparatus at a rate sufficient to enable the continuous feeding in A) to be maintained.

A preferred embodiment includes, in addition to steps A) and B) as described above, the following concurrent operation, namely, continuously, but alternately, withdrawing from at least one and then from at least one other of at least two reaction vessels, an aqueous solution of alkali metal salt of sulfamic acid at a rate that maintains said stream of (ii) in A), and during the time the solution is being withdrawn from said at least one of at least two reaction vessels, forming additional aqueous solution of alkali metal salt of sulfamic acid in said at least one other of at least two reaction vessels from which solution is not then being withdrawn. In this way, aqueous alkali metal sulfamate solution can be continuously withdrawn from one or more tanks ("Tank(s) I") to serve as the continuous feed of (ii) in A), while forming more of such solution in one or more other tanks ("Tank(s) II"), so that when Tank(s) I is/are depleted, the system is switched to Tank(s) II which then serve(s) as the supply for the continuous feed of (ii) in A) until depleted, and by that time more of such solution has been formed in Tank(s) I. Thus by alternating the supply and the production from one tank (or group of tanks) to another tank (or group of tanks) and switching back and forth between the filled tanks as the supply, the continuous feed of the aqueous alkali metal sulfamate solution can be maintained without material interruption.

A particularly preferred embodiment of this invention is a process which comprises:

A) continuously feeding into mixing apparatus (i) a bromine stream and (ii) a separate feed stream of an aqueous solution of alkali metal salt of sulfamic acid identified below in C), in proportions that produce an aqueous product having an active bromine content of at least 100,000 ppm (wt/wt), and an atom ratio of nitrogen to active bromine from (i) and (ii) greater than 1;

B) withdrawing the aqueous product from the mixing apparatus at a rate sufficient to enable the continuous feeding in A) to be maintained; and C) continuously, but alternately, withdrawing from at least one and then from at least one other of at least two reaction vessels, an aqueous solution of alkali metal salt of sulfamic acid at a rate that maintains the stream of (ii) in A), and during the time the solution is being withdrawn from at least one of the reaction vessels, forming additional aqueous solution of alkali metal salt of sulfamic acid in at least one other of the reaction vessels from which solution is not then being withdrawn.

Various types of mixing apparatus can be used in the practice of this invention. In one preferred embodiment the mixing apparatus comprises a static mixer. The static mixer can be of any suitable design and configuration as long as it is capable of continuously receiving the continuous feed streams of bromine and aqueous alkali metal sulfamate solution, and continuously discharging a mixture formed from these feed streams that is substantially uniform in composition and thus satisfies product specifications.

Another preferred mixing apparatus comprises a vessel equipped with a mechanical stirrer. In this case, the vessel continuously receives the continuous feed streams of bromine and aqueous alkali metal sulfamate solution, and either continuously or intermittently discharges a substantially uniform mixture formed from these feed streams. The mechanical stirrer can be programmed to operate continuously or intermittently as long as the discharge from the vessel is constantly substantially uniform in composition. Thus if the discharge from the vessel is intermittent, the incoming continuous feeds are preferably agitated during at least most of the time the vessel is filling up to a predetermined volume at which point the contents of the vessel are discharged more rapidly than the total incoming feeds until the vessel reaches a predetermined low volume, at which point the discharge is discontinued so that the vessel begins to fill up again. On the other hand, if the discharge is continuous, the system is designed and constructed such that the total incoming volume to the vessel and the concurrent outgoing volume from the vessel remain equal and so that the vessel continuously contains a predetermined volume of contents which are being mixed by the mechanical stirrer. In such case, the stirrer preferably is operated continuously.

The processes of this invention are continuous processes and involve continuous feeds to the mixing apparatus. In addition, some embodiments of the invention involve continuous alternate withdrawal of an aqueous solution of alkali metal salt of sulfamic acid from at least one reaction vessel while another quantity of such solution is being formed in at least one other such vessel. In such embodiments the term "continuous" or "continuously" is not meant to exclude interrupted feeds or withdrawals. Generally, if such interruptions occur, they are of short duration and are such as not to materially affect the steady state operation of the overall process, and also are such as not to cause production of a significant quantity of off-specification concentrated product solution. An example of such a slight, non-adverse interruption may occur when switching the flow of aqueous solution of alkali metal salt of sulfamic acid from at least one reaction vessel to another such vessel, an operation which is referred to above as part of a "continuous" feed. As long as such switching operation does not disrupt the operation or result in the formation of a significant quantity of off-specification concentrated product solution, such interruption is acceptable and is within the spirit of the term "continuous". An exception exists where the term "continuous" does not allow for interruption, namely in any case where both continuous and non-continuous (e.g., "intermittent") operation in a given step or operation are both expressly referred to herein. An example of this exception is the embodiment where product is continuously withdrawn from above-referred-to vessel that is equipped with a mechanical stirrer. Such "continuous" withdrawal is not interrupted because in another embodiment expressly referred to herein, the withdrawal of the same product from the same vessel is specifically described as "intermittent". Thus both alternatives (continuous and non-continuous) are expressly referred to in this disclosure.

In a further embodiment of this invention, a method for disinfecting a surface is provided. This method comprises applying to the surface a concentrated liquid biocide composition produced by any of the above embodiments.

The method for disinfecting a surface comprises applying a concentrated liquid biocide composition to the surface to be disinfected. The concentrated liquid biocide composition may be applied to the surface to be disinfected in various ways. The composition may be poured directly onto the surface, sprayed onto the surface, or poured or sprayed onto an applicator which is then brought into contact with the surface. Applicators include, but are not limited to, cloths, sponges, paper towels, and mops.

Yet another embodiment of this invention provides a method of sanitizing a body of water which method comprises introducing into the body of water a concentrated liquid biocide composition. The biocidal composition is produced by the above embodiments.

The method of sanitizing a body of water comprises introducing a concentrated liquid biocide composition [of bromine] into the body of water. A variety of methods may be used to introduce the concentrated liquid biocide composition to the body of water to be sanitized. The concentrated liquid biocide composition may be added directly to the body of water, either all at once or slowly over time, for example via a pump or feeder. In systems in which the water is circulated through an apparatus, the concentrated liquid biocide composition may be added to this apparatus.

The addition of the concentrated liquid biocide composition to the body of water to be sanitized preferably yields a concentration of biocide in the body of water such that in the range of from about 2 to about 10 milligrams per liter of total available halogen, expressed as $Cl_2$, is present in the body of water. In a preferred embodiment, the concentrated liquid biocide composition is introduced into the body of water as required, such that in the range of from about 2 to about 10 milligrams per liter of total available halogen, expressed as $Cl_2$, is maintained within the body of water. A more preferred amount of total available halogen, expressed as $Cl_2$, in the body of water is from about 2 to about 5 milligrams per liter. These concentrations of total available halogen, expressed as $Cl_2$, are known in the art to be sufficient for sanitizing a body of water and for maintaining sanitization of a body of water.

An advantage of this invention is that the concentrated liquid biocide compositions provided herein are at least as effective as bleach as a biocide, without the undesirable properties of bleach, which include instability and an unpleasant odor. Thus, the methods of this invention may replace those which use bleach in biocidal applications. The organisms that may be controlled using the methods of this invention include bacteria, fungi, slime, and mollusks. Another advantage of the methods of this invention is that the concentrated liquid biocide compositions provided herein are water-soluble, non-acidic, and noncorrosive. A further advantage of this invention is that the concentrated liquid biocide compositions provided by this invention are single-feed biocides, the term single-feed signifying that the end user need not do any further mixing of components to produce the concentrated liquid biocide composition.

The following examples are presented for purposes of illustration, and are not intended to impose limitations on the scope of this invention.

EXAMPLES

A general procedure for preparing the compositions of this invention using sulfamic acid involves, as a first step, forming a slurry of sulfamic acid in water. Typically the pH of this slurry is below 1 pH unit. Sodium hydroxide at 50% concentration is then added until the solid is completely dissolved. Additional 50% NaOH is added until the desired pH is reached. Bromine is then added at a rate to allow the bromine to dissolve and react with the sulfamic acid without forming a pool of halogen on the bottom of the reactor. On a laboratory scale, a convenient rate of addition is approximately two drops per second. Sodium hydroxide (e.g., 25% or 50%) is co-fed to the reactor to maintain the desired pH (e.g., in the range of about 12 to about 14, and preferably in the range of 12 to 13.5). It has been found that stable solutions containing as much as 26% active bromine (11.5% on an active chlorine basis) can be prepared by the process of this invention.

Various compositions were prepared using the above general procedure and the active a bromine content of the resultant compositions was determined analytically. The conditions used and results obtained (observations on odor and vapor, and initial contents of active bromine in the solutions) are summarized in Table 1.

TABLE 1

Data on Prepared Sulfamic Acid Stabilized Bromine Solutions

| Ex. No. | Halogen | pH | $SA_{eq}$ | Odor and Vapor Comments | Active $Br_2$, wt % |
|---|---|---|---|---|---|
| A** | $Br_2$ | 7.0 | 1.48 | Slight Br odor, no fuming | 13.4%* |
| B** | $Br_2$ | 7.0 | 1.13 | Moderate Br odor, no fuming | 26.7% |
| 1 | $Br_2$ | 13.0 | 1.42 | Slight sweet smell, no observed vapor | 12.4%* |
| 2 | $Br_2$ | 13.0 | 1.15 | Slight sweet smell, no observed vapor | 19.6% |

$SA_{eq}$ = Sulfamic acid to halogen mole ratio.
*Measured with Hach spectrometer; all others titrated using starch-iodine-sodium arsenite method.
**Comparative Examples.

The specific details for Comparative Example B and Example 2 of Table 1 are given below.

Comparative Example B

Bromine, Caustic and Sodium Sulfamate at Neutral pH

A 500 mL flask was charged with 26.0 g of sulfamic acid and 50 g of water. To this stirred slurry was added 30.9 g of 50% sodium hydroxide, which raised the pH to approximately 12. The sulfamic acid then dissolved into solution. 37.7 g of bromine is fed into the solution until the pH drops to approximately 7, when 50% sodium hydroxide (10.9 g) is co-fed to maintain the pH between 6 and 9. 5 mL of 0.01 N sodium hydroxide was used to bring the final pH to approximately 7±0.5. The contents are then transferred to an amber bottle for storage. Starch-iodine titration of a sample of this solution indicated that it had an active bromine content of 26.7%. Analysis of the solution after six weeks of storage at ambient temperature indicated that the stabilized bromine solution still contained more than 95% of its active bromine content.

Comparative Example C

Bromine, Caustic and Sodium Sulfamate at Several pH's

A 250 mL flask is charged with 94 g of water and 13.6 g of NaOH (0.339 mol). The solution is cooled to 30° C., and then 13 g of sulfamic acid (0.134 mol) is slowly added to the solution. 18.0 g of bromine (0.113 mol) are added while maintaining the temperature of the solution at 30° C. The clear yellow solution is divided into four 35 g portions. The pH of the four portions, is adjusted using concentrated aqueous HCl; each portion to a different pH value. All four portions were stored at 30° C. for 60 days. The pH of each solution had decreased significantly, as had the amount of available halogen. The results are summarized in Table 2.

TABLE 2

| Example | Initial pH | Final pH | Initial available $Cl_2$ | Final available $Cl_2$ | Initial total $Br_2$ |
|---|---|---|---|---|---|
| C-1 | 11.6 | 2.9 | 5.9% | 2.3% | 13.2% |
| C-2 | 10.0 | 2.0 | 4.8% | 3.4% | 10.8% |
| C-3 | 8.0 | 1.8 | 5.7% | 3.6% | 12.9% |
| C-4 | 6.2 | 2.0 | 5.7% | 3.6% | 12.8% |

Example 2

Bromine, Caustic (50% Sodium Hydroxide) and Sodium Sulfamate at High pH

A 500 mL flask was charged with 26.0 g of sulfamic acid and 50 g water. To this slurry was added 35.0 g of 50% sodium hydroxide. As the acid was converted to the sodium salt, it dissolved into the aqueous solution more readily. Bromine (37.0 g) and 50% sodium hydroxide (30.0 g) were co-fed into the solution at a rate which maintained the pH between 11 and 13. After all of the bromine and caustic had been added, the contents were transferred to an amber bottle for storage. Starch-iodine titration of a sample of the solution indicated that it had an active bromine concentration of 19.6%. Analysis of the bromine solution after 6 weeks of storage at ambient temperature indicated that it still contained more than 95% of its active bromine content.

Example 3

Bromine, Caustic and Sodium Sulfamate at High pH

A 250 mL flask was charged with 82.0 g of water and 10.0 g of NaOH (0.250 mol). The solution is stirred, and cooled with an ice bath. 18.0 g of bromine (0.113 mol) is added to the NaOH solution in three aliquots during a ten minute period with stirring. The clear yellow solution is cooled to maintain the temperature at less than 30° C. A separate flask containing 12.0 g of water has 8.6 g of NaOH (0.22 mol) added to it, while maintaining the solution temperature at less than 60° C. with an ice bath. 13.0 g of sulfamic acid (0.134 mol) is then added to this second solution, while still maintaining the temperature at less than 60° C. with an ice bath. This second solution is added to the bromine/NaOH solution. The pH of the combined solution is 12.6, and the bromine content is 11.5%. The solution is stored at 30° C. for 63 days. The pH of the solution had not changed significantly (from 12.6 to 13.0), and neither had the amount of available halogen (from 5.10% to 4.94%).

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated in tow into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing a concentrated, stabilized liquid biocide formulation, which process consists of cofeeding to an aqueous solution formed from components consisting of water, sulfamic acid and alkali metal base, feed components consisting of (i) bromine and (ii) a solution of alkali metal base that maintains, while cofeeding, the pH of said concentrated, stabilized liquid biocide formulation produced in the range of from about 12 to about 14.

2. A process according to claim 1 wherein said concentrated, stabilized liquid biocide formulation contains an amount of bromine that is no more than 26% of active bromine.

3. A process according to claim 1 wherein said biocide formulation has an active bromine content of about 100,000 ppm (wt/wt) or more and an atom ratio of nitrogen to active bromine greater than 1.

4. A process according to claim 1, wherein the pH is up to about 13.5.

5. A process of producing a concentrated liquid biocide composition, which process consists of
    A) continuously feeding into mixing apparatus components consisting of (i) bromine and (ii) an aqueous solution of alkali metal salt of sulfamic acid having a pH of about 1 or more, proportioned to produce an aqueous product (a) having an active bromine content of at least 100,000 ppm (wt/wt), and an atom ratio of nitrogen to active bromine from (i) and (ii) greater than 1, and (b) maintaining the pH of said product in the range of from about 12 to about 14; and
    B) withdrawing said product from said mixing apparatus at a rate sufficient to enable the continuous feeding in A) to be maintained.

6. A process according to claim 5 wherein (ii) in A) is an aqueous solution of the sodium salt of sulfamic acid.

7. A process according to claim 6 wherein said atom ratio is in the range of about 1.1 to about 1.5.

8. A process according to claim 5 wherein said mixing apparatus comprises a static mixer.

9. A process according to claim 5 wherein said mixing apparatus comprises a vessel equipped with a mechanical stirrer.

10. A process according to claim 9 wherein said product is intermittently withdrawn from said vessel.

11. A process according to claim 9 wherein said product is continuously withdrawn from said vessel.

12. A process of producing a concentrated liquid biocide composition, which process consists of
    A) continuously feeding into mixing apparatus components consisting of (i) a bromine stream and (ii) a separate feed stream of an aqueous solution of alkali metal salt of sulfamic acid having a pH of about 12 or more, in proportions that produce an aqueous product (a) having an active bromine content of at least 100,000 ppm (wt/wt), and an atom ratio of nitrogen to active bromine from (i) and (ii) greater than 1, and (b) maintaining the pH of said product in the range of from about 12 to about 14; and
    B) withdrawing said product from said mixing apparatus at a rate sufficient to enable the continuous feeding in A) to be maintained; and
    C) continuously, but alternately, withdrawing from at least one and then from at least one other of at least two reaction vessels, an aqueous solution of alkali metal salt of sulfamic acid at a rate that maintains said stream of (ii) in A), and during the time the solution is being withdrawn from said at least one of at least two reaction vessels, forming additional aqueous solution of alkali metal salt of sulfamic acid in said at least one other of at least two reaction vessels from which solution is not then being withdrawn.

13. A process according to claim 12 wherein said aqueous solution of alkali metal salt of sulfamic acid is an aqueous solution of the sodium salt of sulfamic acid.

14. A process according to claim 12 wherein said aqueous solution of alkali metal wherein said atom ratio is in the range of about 1.1 to about 1.5.

15. A process according to claim 12 wherein said mixing apparatus comprises a static mixer.

16. A process according to any of claim 12 wherein said mixing apparatus comprises a vessel equipped with a mechanical stirrer.

17. A process according to claim 16 wherein in B) said aqueous product is intermittently withdrawn from said vessel.

18. A process according to claim 16 wherein in B) said aqueous product is continuously withdrawn from said vessel.

19. A process according to claim 12 wherein said mixing apparatus comprises a static mixer, and wherein said additional aqueous solution of alkali metal salt of sulfamic acid is formed from an alkali metal base, sulfamic acid, and water.

20. A process according to claim 12 wherein said mixing apparatus comprises a static mixer, wherein said aqueous solution of alkali metal salt of sulfamic acid is an aqueous solution of sodium sulfamate, and wherein said additional aqueous solution of alkali metal salt of sulfamic acid is formed from a water-soluble sodium base, sulfamic acid, and water.

21. A process according to claim 20 wherein said sodium base is an aqueous solution of sodium hydroxide, and wherein the sodium sulfamate is formed as an aqueous solution by charging to a reactor (i) an aqueous solution of sodium hydroxide, and (ii) a slurry of sulfamic acid in water, or (iii) separate charges of sulfamic acid and water, or (iv) both of (ii) and (iii).

* * * * *